United States Patent [19]

Gebhard et al.

[11] Patent Number: 5,126,238
[45] Date of Patent: Jun. 30, 1992

[54] HOLLOW FIBER CELL PROPAGATION SYSTEM AND METHOD

[75] Inventors: Timothy C. Gebhard, Escondido; Uday K. Veeramallu, San Diego, both of Calif.

[73] Assignee: Unisyn Fibertec Corporation, San Diego, Calif.

[21] Appl. No.: 480,533

[22] Filed: Feb. 15, 1990

[51] Int. Cl.$^5$ .......................... C12N 5/00; C12M 3/04; C12M 1/36

[52] U.S. Cl. ...................... 435/3; 435/240.1; 435/240.242; 435/284; 435/289; 435/291; 435/807; 422/82.04; 204/409

[58] Field of Search ............. 435/288, 813, 289, 290, 435/291, 313, 807, 284, 285, 311, 240.1, 240.2, 3, 240.242, 240.241, 41, 240.23, 240.25; 422/82.04; 204/400, 409, 424

[56] References Cited

U.S. PATENT DOCUMENTS

| | | | |
|---|---|---|---|
| 4,220,725 | 9/1980 | Knazek et al. | 435/285 |
| 4,720,462 | 1/1988 | Rosenson | 435/285 |
| 4,764,471 | 8/1988 | Ripka | 435/255 |
| 4,889,812 | 12/1989 | Guinn et al. | 435/289 |
| 4,999,298 | 3/1991 | Wolfe et al. | 435/240.242 |

FOREIGN PATENT DOCUMENTS

| | | | |
|---|---|---|---|
| 0343394 | 11/1989 | European Pat. Off. | 435/284 |
| 6188872 | 10/1984 | Japan . | |
| 1280270 | 12/1986 | Japan | 435/284 |
| 2259580 | 11/1987 | Japan | 435/284 |

OTHER PUBLICATIONS

Schweitzer, *Handbook of Separation Techniques for Chemical Engineers*, 2nd Ed., McGraw Hill, 1988 pp. 2-21, 22.

Seaver, S., Editor, *Commercial Production of Monoclonal Antibodies—A Guide for Scale-Up*, Marcel Dekker, Inc., N.Y., 1987, pp. 119-138.

*Primary Examiner*—Robert J. Warden
*Assistant Examiner*—William H. Beisner
*Attorney, Agent, or Firm*—Edward S. Irons; Thomas S. Hahn

[57] ABSTRACT

A unique hollow fiber bioreactor system and method for the propagation of cells and the production of various cell propagation products is described. The system and method include the use of a flow block holder which allows a dissolved oxygen probe to be calibrated at the same pressure as the media in the bioreactor system.

55 Claims, 7 Drawing Sheets

HOLLOW FIBER CELL PROPAGATION SYSTEM AND METHOD

FIELD OF THE INVENTION

This invention relates to a system and a method for the propagation of cells and to the production of various cell propagation products. More particularly, the invention relates to the propagation of cells in a unique hollow fiber bioreactor system and process.

BACKGROUND OF THE INVENTION

The propagation of suspension and anchorage dependent cells in hollow fiber bioreactors is variously described in the prior art. In general, known procedures entail the use of bioreactors comprising a plurality of media permeable parallel hollow fibers surrounded by an extracapillary space (ECS). Cell growth medium passed through the hollow fiber lumens permeates the lumen walls to support cell growth in the ECS. See, e.g. U.S. Pat. Nos. 3,821,087; 4,439,322 and Ramsay et al. In Vitro 20:10 (1984).

SUMMARY OF THE INVENTION

This invention provides a unique hollow fiber cell propagation system and process. The cell propagation system is compact and highly efficient. It includes a plurality of novel elements including a bioreactor having hollow fibers of unique composition and interrelated means to control dissolved oxygen, basal medium and reagent composition, temperature and pH and waste disposal means.

The process as practiced in the system of the invention provides high cell and product yields with a low consumption of medium and nutrients. These benefits are attributable to a plurality of innovations which individually and in combination provide for the uniquely efficient propagation of suspension and anchorage dependent mammalian, insect, avian, plant and fungal cells and associated products.

DETAILED DESCRIPTION OF THE INVENTION

In the specification, the following symbols have the indicated significance or meaning:

| | |
|---|---|
| DO1 | Dissolved oxygen value upstream of bioreactor(s), expressed as % (percentage of air saturation) |
| DO2 | Dissolved oxygen value downstream of bioreactor(s), expressed as % (percentage of air saturation) |
| $\Delta DO$ | Dissolved oxygen differential: $\Delta DO = DO1 - DO2$ |
| ECS | Extracapillary space |
| Gi | Glucose concentration entering system, expressed in mg/l |
| Go | Glucose concentration exiting system, expressed in mg/l |
| GUR | Glucose utilization rate, expressed in mg/hr Calculated as: $GUR = \frac{v(Gi - Go)}{1000}$ where v = basal medium feed rate |
| Basal Medium Feed Rate | Rate at which basal medium and reagents enter and leave the system. Expressed in ml/hr |
| Lumen (or Loop) | Space inside a hollow fiber |
| Basal Medium | Nutrient medium comprises water, salts, amino acids, vitamins. |
| Reagents | Substances added to a medium and known to have a particular action under certain conditions |
| Plateau Section | Portion of hollow fiber run at which process conditions are stable |
| Growth Factor Mixture | Combination of defined basal medium growth factors and/or serum |
| System Cancellation | Time at which growth support for the hollow fiber system is terminated |

In general, the cell propagation process of the invention may include some or all of the steps 1 to 14 described hereinafter.

1. Cell lines are grown in several different basal medium and reagent types and combinations in order to select the most appropriate growth medium for the hollow fiber run. The selected growth medium is reduced to the simplest practical form.

2. Following hollow fiber system sterilization and assembly, basal medium is fed into the system and temperature control is set at about 37° Celsius.

3. Target Go values, preferably in a range of 50–500 mg/l and GUR (range is product and cell line dependent) values are selected for the plateau section of the run.

4. Gas composition ($CO_2$, $N_2$, air) is selected for system start up based upon pH requirements and cell line sensitivity to $O_2$. These gases are blended and humidified to approximately 100% relative humidity before delivery to the oxygenator.

5. Loop circulation rates are established which will support bioreactor oxygen demands generated by targeted GURs. DO2 values are preferably held above 10% saturation of air by lumen flow selection.

6. ECS growth factor mixture is formulated based upon historical experimentation. ECS growth factor delivery and product harvest program is developed as a function of targeted GUR, feedback inhibition data, cell line and product requirements. ECS growth factor delivery and product harvest program is entered into the programmable controller.

7. Basal medium feed rate is set by adjusting the basal medium feed pump. The initial feed rate may be set high (in excess of that required for the targeted GUR) to provide accelerated generation of cell mass.

8. A cell inoculum is introduced into the ECS of the bioreactor(s). Cell count of the inoculum is cell line and bioreactor surface area dependent.

9. As target Go and GUR are approached, basal medium feed rates are reduced step-wise until target Go and GUR values are reached substantially simultaneously.

10. $CO_2$ flows are gradually reduced as target GURs are reached to maintain pH values in preferred ranges.

11. Productivity (protein production) is correlated with $\Delta DO$ values.

12. GURs are held constant by fine adjustments in basal medium feed rate and system reagent composition.

13. Aerobic efficiency of the system is monitored by the ratio of $GUR/\Delta DO$ and as it relates to product output. System cancellation is determined by comparing these values to established limits developed through production cost analysis.

14. Data generated by the run may be added to the general data base and used to further define parameters such as optimal operational GURs, $\Delta DOs$, ECS programming (growth factor delivery frequency, product harvest frequency and volume) and reagent recipes in future runs.

The system in which this process may be practiced is schematically illustrated by FIGS. 1 to 7.

THE SYSTEM OF THE INVENTION

Figure 1:
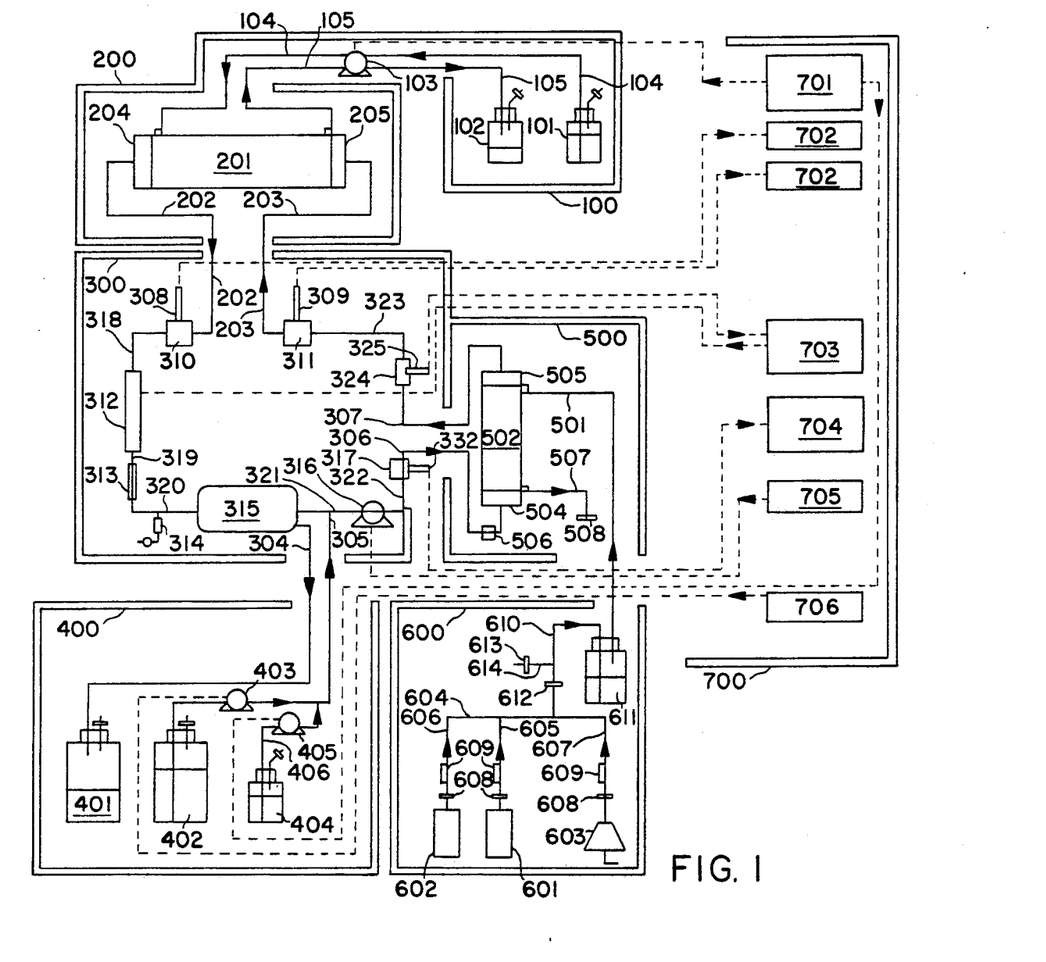
FIG. 1 is a schematic illustration of the cell propagation system of the invention.

As shown in FIG. 1, the system includes interconnected ECS product/feed section 100, reactor section 200, loop section 300, loop feed/waste section 400, oxygenator section 500, gases section 600 and electronics section 700. The system preferably takes the compact form shown by FIG. 8 in which various of the system elements are mounted on a plastic, preferably transparent polycarbonate mounting sheet.

THE ECS PRODUCT/FEED SECTION

The ECS product/feed section 100 includes an ECS feed reservoir 101, an ECS product reservoir 102, and an ECS pump 103. ECS feed reservoir 101 is connected by line 104 to the pump 103, and the reactor section 200. ECS product is connected by lines 105 to the pump 103 and the reactor section 200.

THE REACTOR SECTION 200

The reactor section 200 includes a hollow fiber bioreactor 201 connected through lines 104 and 105 to the ECS product/feed section 100 and through lines 202 and 203 to the loop section 300. The bioreactor 201 is provided at each end with manifolds 204 and 205 to which lines 202 and 203 are connected.

THE LOOP SECTION 300

The loop section 300 is connected through lines 202 and 203 to the reactor section 200; through the lines 304 and 305 to the loop feed waste section 400; and, through lines 306 and 307 to the oxygenator section 500. The loop section 300 includes two dissolved oxygen probes 308 and 309 with associated dissolved oxygen probe flow blocks 310 and 311, a loop heater 312, a loop flowmeter 313, a loop sampler 314, a loop reservoir 315, a loop circulation pump 316, and a pH probe 332 and pH probe flow block 317.

The dissolved oxygen flow block 310 is connected by line 202 to the reactor section 200 and by line 318 to the loop heater 312 which is connected by the line 319 to the loop flowmeter 313. The flowmeter is connected by line 320 to the loop reservoir 315. The line 320 is fitted with a loop sampler 314.

Loop reservoir 315 is connected by line 321 to loop circulation pump 316. The loop Section 300 which is connected through lines 306 and 307 to the oxygenator section 500. A pH probe 332 and pH probe flow block 317 are located in line 322.

The dissolved oxygen probe flow block 311 is connected to the reactor section 200 by the line 203 and by the line 323 to the resistance temperature detector (RTD) probe flow block 324 having an associated RTD probe 325. The RTD probe flow block 324 is connected by the line 307 to the oxygenator section 500.

THE LOOP FEED/WASTE SECTION 400

The loop feed/waste section 400 is connected by the lines 304 and 305 to the loop section 300. It includes a waste reservoir 401 connected to the loop reservoir 315 through the line 304; a basal medium feed reservoir 402 connected to the line 305 through the loop feed pump 403; and a glucose reservoir 404 connected by the line 406 through the glucose feed pump 405 to the line 305.

THE OXYGENATOR SECTION 500

The oxygenator section 500 is connected by lines 306 and 307 to the loop section 300 and by the line 501 to the gases section 600. The oxygenator section 500 includes a hollow fiber oxygenator 502 having manifolds 504 and 505. The manifold 505 is connected to the line 307 from the loop section 300. The line 306 is fitted with a loop filter 506 positioned before the manifold 504. Oxygenator exhaust line 507 is provided with an exhaust filter 508.

THE GASES SECTION 600

The gases section 600 is connected to the oxygenator section 500 by the line 501. It includes a source of nitrogen, e.g., a cylinder 601, a source of carbon dioxide, e.g., a cylinder 602, and an air pump 603, each connected to manifold line 604 by lines 605, 606 and 607, respectively. Each of lines 605, 606 and 607 is fitted with an oil/particle gas filter 608 and a gas flowmeter 609.

Manifold line 604 is connected through line 610 to gas humidifier 611. The line 610 has an in-line gas feed filter 612. A humidifier water fill ;line 614 with an in-line filter 613 is attached to line 610.

THE ELECTRONICS SECTION 700

The electronics section 700 includes a programmable controller 701, dissolved oxygen monitors 702, a temperature monitor and controller 703, a pH monitor 704, a loop circulation pump controller 705, and a basal medium feed pump controller 706. These electronic components are functionally interconnected with several relevant sections of the system as shown by the broken lines in FIG. 1.

The electronic elements, per se, are commercially available items. The component interconnections are made in a known manner and can readily be accomplished by the skilled person.

DETAILED DESCRIPTION OF CERTAIN SYSTEM ELEMENTS

Except as specifically described herein, the various elements of the system depicted by FIG. 1 are of conventional design.

1. The Hollow Fiber Bioreactor 201

Hollow fiber bioreactors useful in the invention may be of known design. See, e.g., U.S. Pat. Nos. 4,804,628; 3,821,087; and 4,391,912.

A preferred hollow fiber membrane and bioreactors including such hollow fiber membranes are described in co-pending application of Gebhard and Veeramallu, Ser. No. 355,590, filed June 3, 1989, now abandoned. Permeable membranes useful in the bioreactors of this invention may be selected to accommodate the particular cell propagation process or method in which the reactor is to be used. Various types of semipermeable membranes are known. Such semi-permeable membranes may be cellulosic or of synthetic origin. Polysulfone, polymethyl, methacrylate and blends of isotactic and syndiotactic polymethyl methacrylate are appropriate. Semi-permeable hollow fibers of the kind described in U.S. Pat. No. 3,896,061 incorporated herein by reference are appropriate.

A preferred form of hollow fiber bioreactor is a dialysis device sold by Toray Industries, Tokyo, Japan.

2. The Dissolved Oxygen Probe and Probe Flow Block

Figure 2:
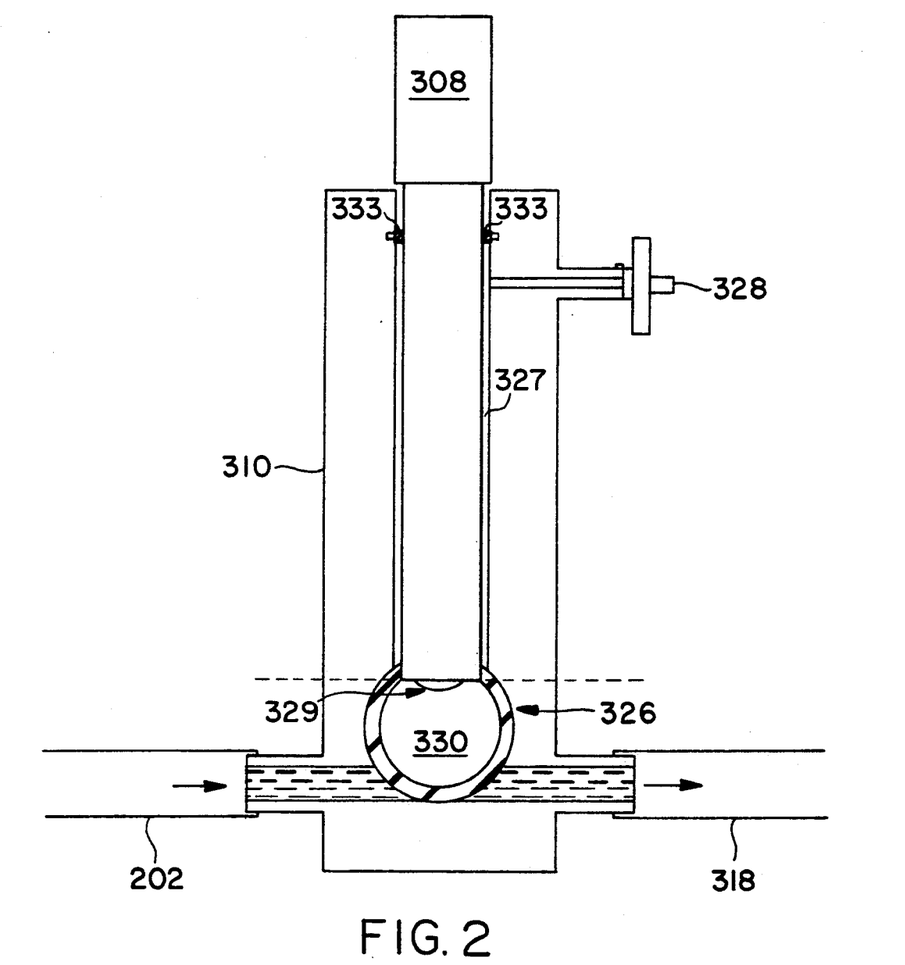
FIG. 2 is a sectional view of a dissolved oxygen probe and probe block useful in the system of the invention.

FIG. 2 schematically illustrates a dissolved oxygen probe 308 and associated flow block 310. As shown, these components include the dissolved oxygen probe 308 and the flow cell body 310 which functions as a flow block. Medium from the reactor section 200 enters the flow cell body 310 through the line 202. Fluid exits through the line 318. The dissolved oxygen probe 308 is fitted to the body 310 by the O-ring 333. A teflon membrane 329 is fitted to the distal end of the probe 308. An observation window 330 fitted with an O-ring seal 326 is provided. The annular space 327 between the probe 308 and the body 310 is provided with an appropriate, e.g., 0.2 $\mu$m, filter 328.

The dissolved oxygen probe and associated flow block permits on-line measurement of the dissolved oxygen content of the media. As shown in FIG. 1, one such device 309, 311 is positioned to measure the DO1 of the media prior to entry into the bioreactor 201 and a second such device 308, 310 measures media DO2 after passage through the bioreactor. In use, an air bubble is introduced sterilely through the filter 328 to displace medium below the teflon membrane 329 of the dissolved oxygen (DO) probe 308. The loop flow channel is arranged such that flow continues through the flow cell, as shown in FIG. 2, through lines 202, the flow cell and line 318. Because the medium flow is maintained during introduction of the air bubble, the pressure in the bubble is consistent with that of the medium flowing through the loop.

Upon completion of the calibration, the air bubble is removed through the filter 328 and the filter sealed closed. The observation window 330 is provided to permit monitoring of the entire calibration process and of the integrity of the DO probe membrane 329.

Commercially available DO probes may be utilized. A preferred galvanic dissolved oxygen probe is available from Phoenix Electrode, 6103 Glenmont, Houston, Tex. 77081, as item 025NG-15-80. The DO probe is appropriately connected to the electronic DO monitor 702.

Aerobic Efficiency

Aerobic efficiency is determined by simultaneously measuring the GUR of the bioreactor and the dissolved oxygen differential ($\Delta$DO) across the bioreactor and using the value GUR/$\Delta$DO to assess the performance of the bioreactor in terms of product formation; product formation and GUR/$\Delta$DO relationships having been established through historical performance. For these values to have significance, other system operating parameters must be taken into account such as loop circulation rate, basal medium type, temperature and Go. For example, using a murine hybridoma system as a model with a loop circulation rate of 350 ml/hr, Dulbecco's Modified Eagles high glucose [4500 mg/l]medium as the basal medium, a temperature of 37° C., and a Go value of 400 mg/l, GUR/$\Delta$DO values of 3 to 6 (mg/hr) % air saturation indicate an aerobically efficient bioreactor with acceptable product output while GUR/$\Delta$DO values of 10 to 12 mg/hr) % air saturation indicate a reactor with significant oxygen mass transfer problems, low productivity and potential for system cancellation.

Real time verification of cell metabolism in the bioreactor is provided by using the $\Delta$DO value as an indication of the oxygen consumed in the process of respiration. This method of metabolism verification is of exceptional value when a continuity of $\Delta$DO has been established. Deviations to the established $\Delta$DO continuity enable the system operator to immediately take appropriate corrective action without reconducting time consuming off line assays.

3. The Hollow Fiber Temperature Control System

Figure 3:
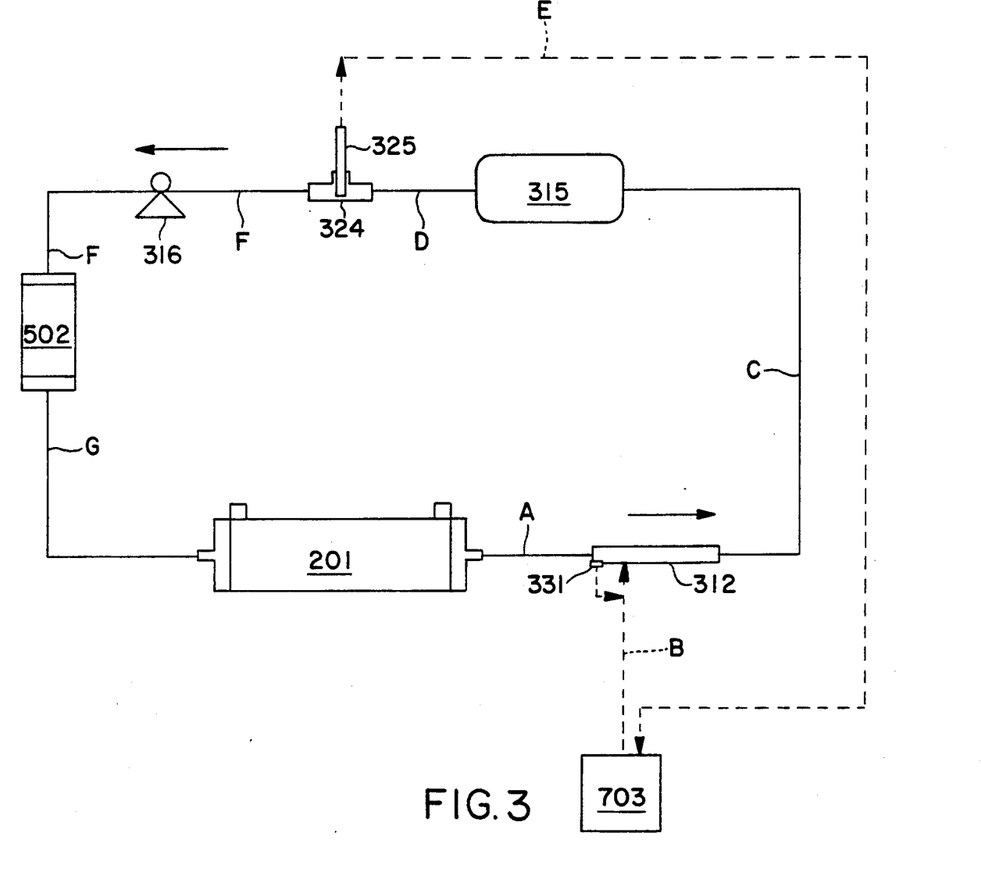
FIG. 3 is a schematic view of a means, useful in the invention for control of the temperature of the basal medium and reagents utilized in the system of the invention.

FIG. 3 is a schematic depiction of a preferred hollow fiber temperature control system useful in the invention.

As shown in schematic FIG. 3, the hollow fiber bioreactor 201 is connected by the line A to the loop heater 312 which is connected by broken line B to the electronic temperature monitor and controller 703. A thermostat 331 is fitted between the heater 312 and the line B.

The heater 312 is connected by the line C to the loop reservoir 315 which is connected by line D to the resistance temperature detector (RTD) probe block 324 and associated RTD probe 325. The RTD probe 325 is connected by the broken line E to the temperature monitor and controller 703. Line F connects the RTD probe flow block, through the loop circulation pump 316, to the oxygenator 502 which is connected by line G to the bioreactor 201.

As FIG. 3 shows, loop temperature is monitored by an (RTD) probe 325 inserted into the loop. The RTD probe 325 is coupled to the electronic monitor and controller 703. The controller 703 compares the signal from the RTD probe 325 to a preselected set point and makes adjustments accordingly to a heater 312, preferably mounted externally to a stainless steel portion of the loop.

4. The Basal Medium and Reagent Control System

Figure 4:
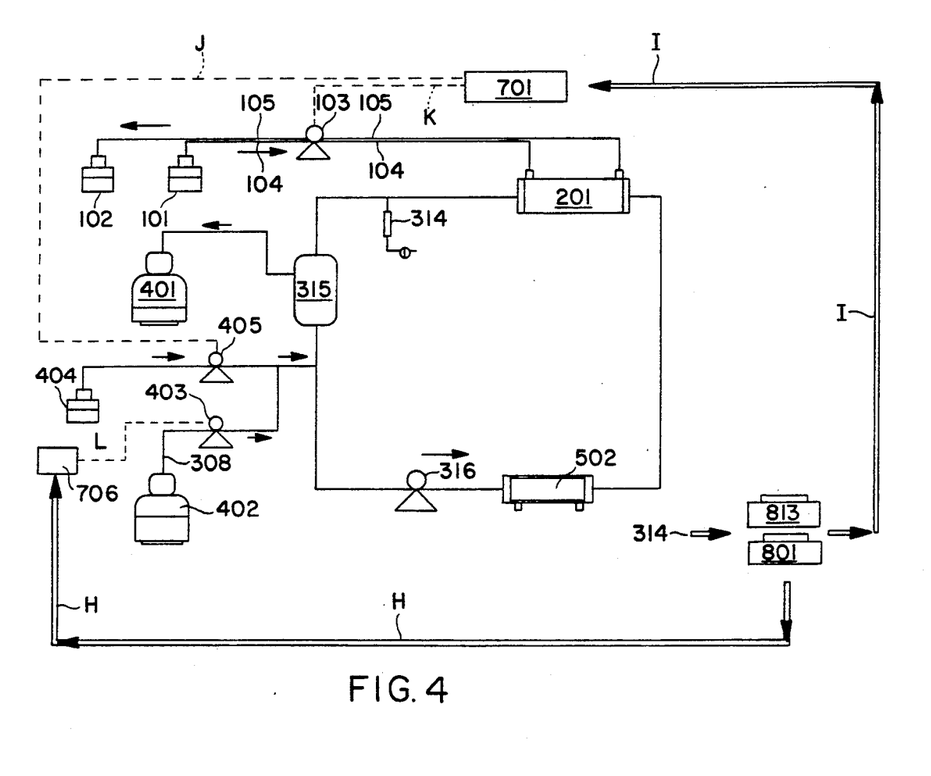
FIG. 4 is a schematic view of a means useful to control the composition of the basal medium and reagents utilized in the system. -.

The basal medium and reagent control system is schematically shown by FIG. 4. Glucose and ammonia analyzer 801 and lactate analyzer 813 are coupled by line H to the basal medium feed pump controller 706 and by line I to the programmable controller 701. The basal medium feed pump controller 706 is coupled by broken line L to the basal medium feed pump 403. The programmable controller 701 is coupled by broken line J to the glucose feed pump 405 and by broken line K to the ECS pump 103.

The glucose and ammonia analyzer 801 is an off line analyzer with multiple dry film based chemistry functions. Samples taken from the loop sample port 314 are manually transferred to the analyzer 801 for glucose and ammonia analysis. Glucose and ammonia assays must be performed independently on the form of analyzer shown.

The off line lactate analyzer 813 consists of a spectrophotometer and analytical means designed specifically for the quantification of lactate through spectrophotometric analysis. Samples taken from the loop sample port 314 are manually transferred to the lactate analyzer 813 for lactate analysis.

Data provided by line H from the analyzers 801 and 813 to the basal feed medium pump controller provides information useful to achieve either manually as shown, or by automation, introduction of basal medium into the loop at a rate required for a preselected GUR. Preselection of the GUR is based on historical data obtained with a similar hollow fiber system. Data provided by the line I to the programmable controller 701 achieves introduction of glucose into the loop at a rate required to maintain a specific Go and preselected GUR.

5. The Waste Disposal System

Figure 5:
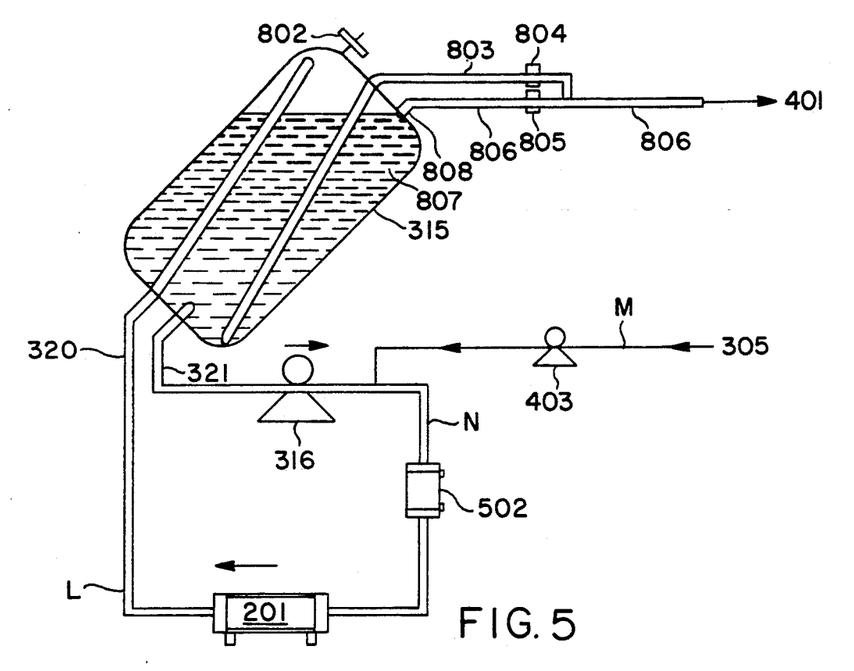
FIG. 5 is a schematic view of a waste disposal system useful in the invention.

A waste disposal system useful in the invention is schematically shown in FIG. 5.

As shown in FIG. 5, the bioreactor 201 is part of a loop which originates and terminates in the loop reservoir 315. Medium feed line M is connected to the loop line N. Loop pick-up line N extends through the loop circulation pump 316 to the hollow fiber oxygenator 502. Line O connects the oxygenator 502 to the hollow fiber reactor 201. As shown, the line L extends into the medium reservoir 315 and terminates at a point above the level of the medium 807 contained therein.

Drain line 803 extends from near the bottom of reservoir 315, through the drain line clamp 804 to a connection with the waste line 806 which extends from the waste exist port 808 at the top of the reservoir 315 and which is provided with waste line clamp 805. A normally closed 0.2 μm filter vent 802 is located on the reservoir above the drain line 803.

A waste displacement system is thus provided, whereby volumes of fresh basal medium entering the loop through line M automatically displace substantially identical volumes of spent medium in the loop through a waste exit port 808 and into waste line 806. Clamp 805 is open during normal operation. Siphoning, caused by venting across the oxygenator membranes, is prevented by the level of medium 807 falling below waste exit port 808 and causing a siphon break.

Reservoir drain line 803 is provided to allow for draining of the reservoir medium. To drain the reservoir 315, the normally closed drain line clamp 804 is opened and the normally open waste line clamp 805 is closed and the normally closed 0.2 μm filter vent 802 is opened. The reservoir can then be drained by siphon.

6. The Oxygenator

Figure 6:
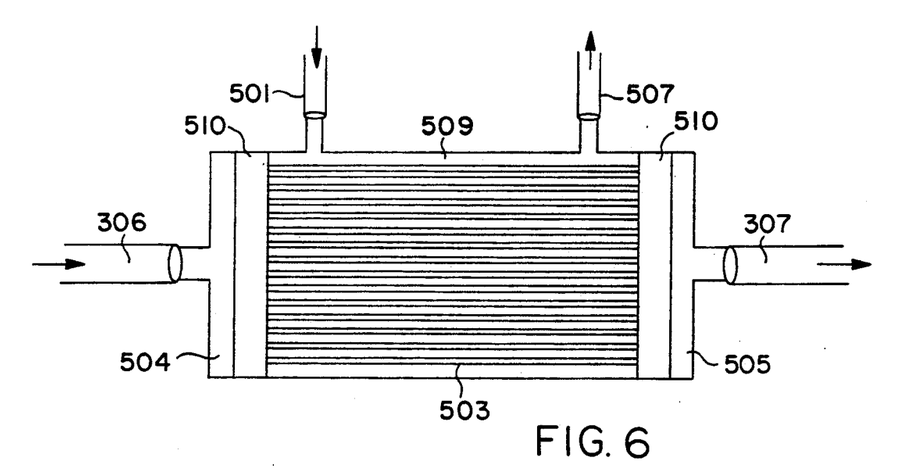
FIG. 6 is a schematic view of an oxygenator useful in the system of the invention.

FIG. 6 schematically illustrates the hollow fiber oxygenator. As shown in FIG. 6, oxygen depleted medium travels through loop line 306 which is coupled to oxygenator manifold 504. Medium then enters a plurality of hollow fibers 503 formed, e.g., from polypropylene held in place by potting material 510. Gases, usually air, nitrogen and carbon dioxide, are blended, humidified, particulate and sterile filtered prior to entering the ECS 509 of the oxygenator through line 501. Gas exchange occurs across the hollow fiber membranes causing the dissolved gases in the medium to come into equilibrium with the gas mixture introduced into the ECS 509. Oxygen replenished medium exits the hollow fibers 503 and then collects in manifold 505 and is delivered to loop line 307. Depleted ECS gases exit the oxygenator ECS 509 through oxygenator exhaust line 507. The air functions primarily as an oxygen source, nitrogen is useful to reduce oxygen levels and thus ameliorate oxygen toxicity problems and carbon dioxide functions as a pH control agent.

7. The Loop Heater

Figure 7:
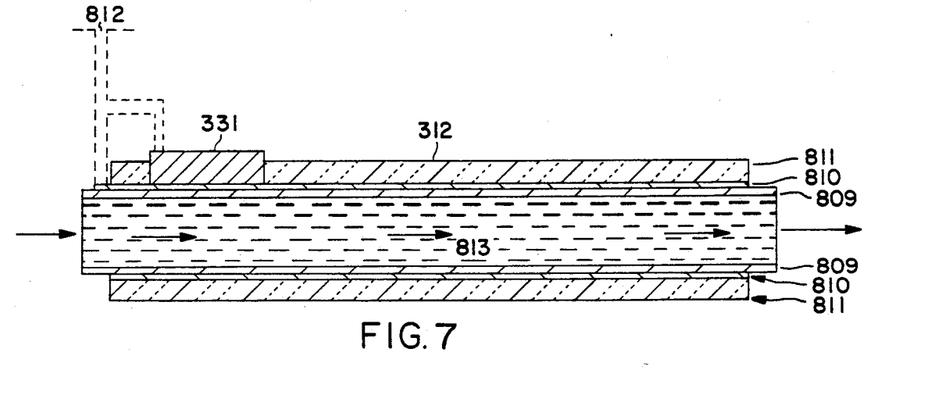
FIG. 7 is a sectional view of a loop heater useful in the system of the invention.

A preferred form of the loop heater 312 is shown in cross-section by FIG. 7. As illustrated, the heater comprises a stainless steel tube 809, an etched foil resistance heating element 810 and appropriate insulation 811. The heater is provided with suitable wiring 812 and a thermostat 331 as a safety feature. The medium 813 passes through the tube 809 in a flow direction indicated by arrows.

8. Single Bioreactor System

Figure 8:
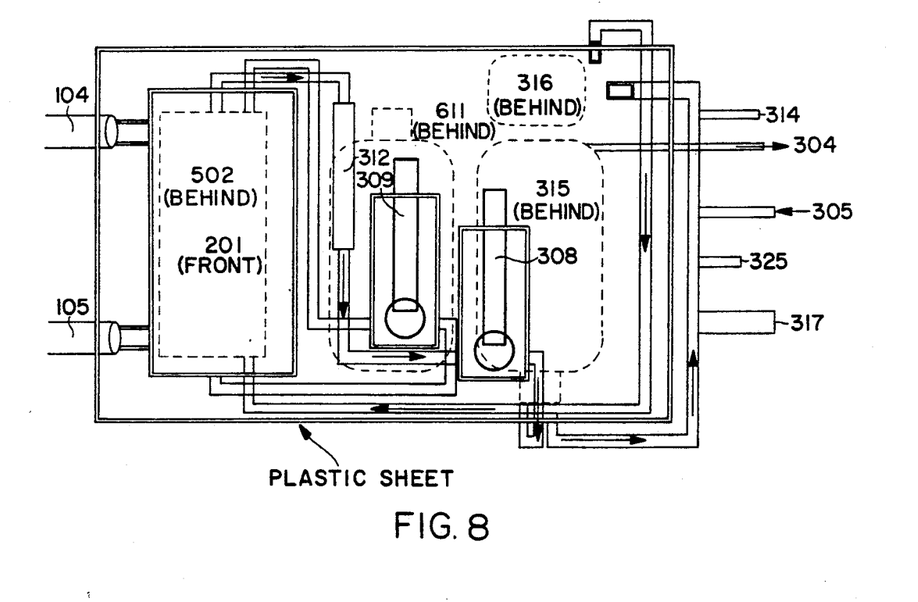
FIG. 8 is a schematic illustration in three dimensions of an integrated, compact configuration of a single reactor system which embodies the invention. Elements shown in broken line are positioned behind elements shown in solid line. All elements are directly or indirectly mounted on the transparent polycarbonate mounting sheet.

A preferred form of compact single bioreactor system configuration is shown by FIG. 8. In the figure, elements shown in broken line are positioned behind elements shown in solid lines. All elements are directly or indirectly mounted on the transparent polycarbonate or similar sheet.

THE METHOD OF THE INVENTION

The method of the invention is described in general by reference to the figures.

Typical ECS feed material is placed in the ECS feed reservoir 101. As heretofore described, such material may comprise basal medium, growth factors and/or serum.

Typical basal feed material as heretofore described is placed in the basal feed reservoir 402. Such material may comprise basal medium, L-glutamine and antibiotics.

A glucose solution, preferably an aqueous solution contained from about 150 g/l to about 250 g/l glucose, is placed in glucose reservoir 404.

A cell line such as murine hybridoma cell line is propagated in the system as follows: The system excluding the oxygenator 502 and bioreactor 201 is sterilized by autoclaving. Presterilized oxygenator 502 and bioreactor 201 are incorporated into the loop under a laminar flow hood. Following assembly, the system is placed in a chamber designed specifically to provide system support functions. Electronic cables (broken lines) are provided which connect the loop circulation pump 316, pH probe 332, dissolved oxygen probes 308 and 309, RTD probe 325 and loop heater 312 to the I/O panel of the control chamber. ECS pump 103, basal medium feed pump 403, and glucose feed pump 405 are provided as functional components of the chamber. The oxygenator gas feed line 501 is connected to a chamber port which provides the appropriate premixed gases. Basal medium feed reservoir 402, waste reservoir 401, glucose reservoir 404, ECS feed reservoir 101 and ECS product reservoir 102 having had their contents adjusted appropriately are connected to the system now in place in the chamber.

Once the aforementioned connections have been made the loop section 300 is filled by clamping the loop line 321 downstream of the loop reservoir and activating the basal medium feed pump 403. This action causes the loop to fill in one specific direction and results in a priming of the loop circulation pump 316. The clamp is opened after the loop is completely filled and the loop reservoir 315 is one third filled. At this point the loop circulation pump 316 is activated and the loop circulation flow rate typically set at 400 ml/min for a bioreactor with 2.0 $m^2$ surface area. Concurrent with this activity the ECS of the bioreactor 201 is filled by manually overriding the ECS control program at programmable controller 701. The ECS pump 103 is activated to pump ECS medium into the bioreactor thereby displacing air from the ECS into the ECS product reservoir 102. This action is continued until the ECS is completely filled with medium. After filling the ECS, the ECS control program is reinstated. The rate of ECS feed and product removal is dependent upon bioreactor surface area, product stability, specific nutrient requirements, and targeted GUR. The maintenance of GO at about one millimolar is appropriate. Simultaneous introduction of growth factor mixture into and removal of product from the ECS at rate that do not differ by more than about five percent is achieved by the programmable controller 701 directing the ECS pump 103. A typical rate of ECS feed and product removal for a murine hybridoma in this system format is 60 ml/day. The ECS product reservoir is collected and replaced as required.

Dissolved oxygen probes 308 and 309 are calibrated by the method described under *Detailed Description of Certain System Elements*. The DO probes 308 and 309 are calibrated biweekly as part of regular system maintenance. A sample of loop medium is taken from the loop sampler 314 and used to make an off line temperature determination. The temperature controller 703 is adjusted to the off line measured value. At this point the loop heater 312 function is activated by setting the heat control set point. A set point is selected which will maintain a constant system loop temperature of 37° C. Another sample of loop medium is taken from the loop sampler 314 and used to make an off line pH measurement. The pH monitor 704 is then adjusted to be consistent with the off line measured value.

Figure 9:
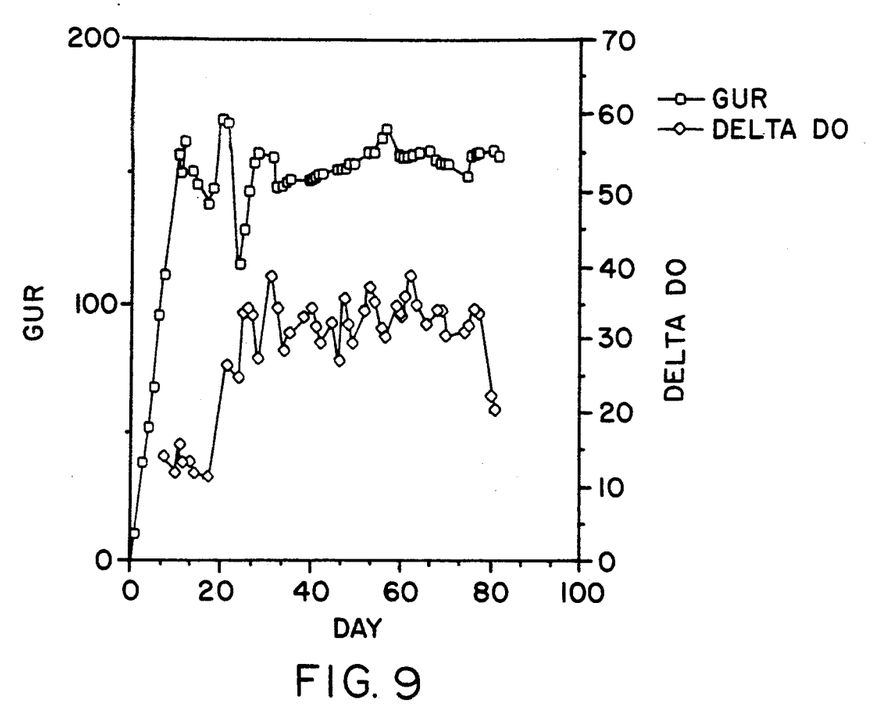
FIG. 9 is a graph which illustrates the parallelism between GUR and $\Delta DO$ in a relatively aerobic system run.

After the aforementioned process parameters have been established the system is allowed a 48 hour check period during which time the probes are allowed to stabilize, system function is verified, and sterility is verified. The basal medium feed pump controller 706 is adjusted to deliver approximately 3 liters of basal medium to the system over the 48 hour check period to serve as a system flush and to remove packing fluids from the bioreactor. Upon completion of the 48 hour check period, an inoculum of hybridomas is prepared. The inoculum generally consists of approximately $2 \times 10^8$ cells/$m^2$ surface area which are suspended in a growth factor mixture which is in turn placed in the ECS feed reservoir 101. The ECS control program is manually overridden to allow for transfer of the inoculum from the ECS feed reservoir 101 through line 104 to the ECS of the bioreactor 201. After completion of the inoculation process, a new ECS feed reservoir 101 containing growth factor mixture is exchanged for the empty inoculation reservoir. A new ECS product reservoir 102 is put in place at this point. Immediately following inoculation, the rate of basal medium delivery to the loop is set by adjusting the basal medium feed pump controller 706 to a value selected on the basis of bioreactor surface area, basal medium type, cell line requirements and targeted GUR. A typical basal medium feed rate for a murine hybridoma with a targeted plateau GUR of 150 mg/hr is 42 ml/hr in a bioreactor with 2.0 $m^2$ surface area available using Dulbecco's Modified Eagles high glucose medium. Glucose addition as a function separate from basal medium is optional in this system format and requires programming the programmable controller 701 to affect the correct delivery of glucose from the glucose feed reservoir 404 to the loop via the glucose feed pump 405. Typical concentrations of glucose in the glucose feed reservoir 404 range between 150 g/l to 300 g/l. Separation of glucose addition allows for greater control of Go and subsequently greater process control. Go values as outlined above with glucose contained in the basal medium settle in a range of 240 mg/l to 400 mg/l. Go values as outlined above with glucose addition separate from basal medium feed can be controlled as low as 50 mg/l. Go samples are taken every 24–48 hrs from the loop sampler port 314 for off line analysis. Significant plateauing of GUR and $\Delta$DO values occur approximately 10 days after inoculation. At this point basal medium feed rate and/or glucose feed rate may undergo fine adjustments to help stabilize GURs. See FIG. 9.

Figure 10:
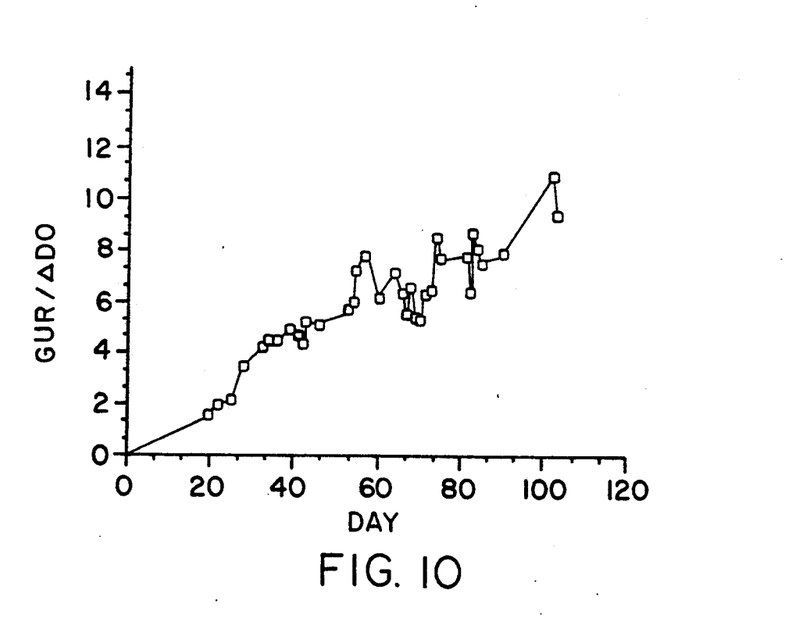
FIG. 10 is a graph which illustrates the gradual decrease in aerobic efficiency of a bioreactor during a 110 day system run.

After plateauing, GUR in the predescribed format can remain constant without further system adjustments for 65–85 days with diligent system maintenance. $\Delta$DO values serve as a real time verification of system performance by providing an instantaneous assessment of the metabolic state of the cell mass without performing off line assays and provide a method to instantaneously assess protein production. $\Delta$DO values are used to monitor the onset of performance problems associated with mass transfer limitations which affect aerobic efficiency. The time of onset of these problems is dependent upon cell type, reactor size, and plateau GUR values. The system parameters set forth here would normally incur significant performance loss due to mass transfer limitations at approximately day 70. Aerobic efficiency of the system is determined by the value GUR/$\Delta$DO where productive plateau values fall in a range of 3–6(mg/hr)/% air saturation and system cancellation is affected when this value reaches 10–12 (mg/hr)/% air saturation. See FIG. 10.

EXEMPLIFICATION OF THE INVENTION

Example I

The propagation of an anchorage dependent type cell line in the invention is described in this example. The cell line is a Crandall feline kidney (CRFK) Dixon strain fibroblast that persistently sheds feline immunodeficiency virus (FIV) and associated proteins The product of interest in the culture supernatant is a viral core glycoprotein p28, quantified by enzyme linked immunoadsorbent assay (ELISA).

The culture system was sterilized, assembled, connected to accessories and chamber controls, primed and flushed, as generally described in "The Method of the Invention" section.

The process parameters in the culture system were set to establish start up conditions. The set point for the temperature controller 703 was set at 37° C. The gas flow meters 609 were adjusted such that the pH monitor 704 read 7.25, and the DO monitors 702 read about 70% air saturation. The loop circulation controller 705 was set to obtain a loop circulation rate of 400 ml/min. The programmable controller 701 was set to deliver ECS feed medium (and collect ECS product) at a frequency of 6 times/day and a volume of 50 ml/day.

An inoculum containing $4.5 \times 10^8$ cells was pumped into the ECS of the bioreactor 201 as generally described in "The Method of the Invention" section. A 2.0m$^2$ surface area bioreactor (model FC-20, Toray Industries) 201 was used in this run. The growth factor mixture comprised 40% fetal bovine serum, 2% L-glutamine, 1% penicillin streptomycin, in Dulbecco's Modified Eagle's (DME) high glucose (4500 mg/l) basal medium. This composition was maintained throughout the run. The ECS feed reservoir 101 and ECS product reservoir 102 were replaced three times/week throughout the run.

The basal medium feed pump controller 706 was set to deliver 41 ml/hr. The basal feed medium comprised 2% L-glutamine, 1% penicillin streptomycin, in DME high glucose basal medium. This composition was maintained throughout the run. Thus, the optional separate glucose feed system was not used in this run. The basal medium feed reservoir 402 was replaced 3 times/week, and the waste reservoir 401 was replaced when necessary.

Samples were withdrawn regularly for off line glucose analysis, as generally described in "The Method of the Invention" section. As Table 1 shows, the glucose utilization rate (GUR) and the dissolved oxygen differential across the bioreactor ($\Delta DO$) both increased as the cells proliferated in the ECS of the bioreactor 201.

TABLE 1

| Day # | GUR (mg/hr) | $\Delta DO$ (%) | p28 (μg/day) |
|---|---|---|---|
| 1 | 10.000 | | |
| 2 | 15.000 | | |
| 3 | 15.600 | | |
| 4 | | | |
| 5 | | | |
| 6 | 32.700 | | |
| 7 | 28.500 | 0.300 | |
| 8 | 41.700 | 0.600 | 150.000 |
| 9 | 44.200 | 1.500 | |
| 10 | 48.100 | 2.200 | 100.000 |
| 11 | | | |
| 12 | | | |
| 13 | 51.280 | | 350.000 |
| 14 | 50.600 | | |
| 15 | 47.200 | 9.900 | 350.000 |
| 16 | 47.200 | 13.500 | |
| 17 | 52.400 | 14.100 | 375.000 |
| 18 | | | |
| 19 | | 16.000 | |
| 20 | 59.500 | 15.800 | 500.000 |
| 21 | 66.000 | 14.800 | |
| 22 | 61.500 | 13.800 | 300.000 |
| 23 | 63.500 | 14.400 | |
| 24 | 67.300 | 14.200 | 300.000 |
| 25 | 67.900 | 15.600 | |
| 26 | | | |
| 27 | | 23.800 | |
| 28 | 71.800 | 21.100 | 360.000 |
| 29 | 60.300 | 22.400 | |
| 30 | 51.900 | 22.400 | |
| 31 | 55.100 | 21.400 | 292.000 |

The target GUR was set at 60 mg/h. By day 13 the GUR and p28 protein production stabilized significantly. The production phase that followed was maintained for almost three weeks. The GUR, p28 production and $\Delta DO$ profiles were all relatively stable and parallel during this period.

The goals of this run were to demonstrate an ability to culture this anchorage dependent cell line in the invention, and to manufacture enough viral p28 protein to meet in house research requirements. Having met these objectives, the run was terminated.

EXAMPLE II

The propagation of a suspension type cell line in the invention is described in this example. The cell line is a murine hybridoma that secretes monoclonal antibodies against transmissible gastro enteritis virus (TGEV). The IgG$_{2a}$ antibody product in the culture supernatant is measured by radial immuno diffusion (RID) assay.

The culture system was sterilized, assembled, connected to accessories and chamber controls, primed and flushed, as generally described in "The Method of the Invention" section.

The process parameters in the culture system were set to establish start up conditions. The set point for the temperature controller 703 was set at 37° C. The gas flow meters 609 were adjusted such that the pH monitor 704 read 7.31, and the DO monitors 702 read about 95% air saturation. Nitrogen flowrate in this run was set to zero. The loop circulation controller 705 was set to obtain a loop circulation rate of 350 ml/min. The programmable controller 701 was set to deliver ECS feed medium (and collect ECS product) at a frequency of 6 times/day and a volume of 24 ml/day.

An inoculum containing $3.1 \times 10^8$ cells was pumped into the ECS of the bioreactor 201 as generally described in "The Method of the Invention" section. A 2.0m$^2$ surface area bioreactor (model FC-20, Toray Industries) 201 was used in this run. The growth factor mixture comprised 35% fetal bovine serum, 1% penicillin streptomycin, in DME high glucose basal medium. This composition was maintained throughout the run. The ECS feed reservoir 101 and ECS product reservoir 102 were replaced three times/week throughout the run.

The basal medium feed pump controller 706 was set to deliver 50.4 ml/hr. The basal feed medium comprised 2% L-glutamine, 1% penicillin streptomycin, in DME high glucose basal medium. This composition was maintained throughout the run. Thus, the optional separate glucose feed system was not used in this run. The basal medium feed reservoir 402 was replaced 3 times/week, and the waste reservoir 401 was replaced when necessary.

Samples were withdrawn regularly for off line glucose analysis, as generally described in "The Method of the Invention" section. As Table 2 shows, the GUR and $\Delta DO$ both increased as the cells proliferated in the ECS of the bioreactor 201.

TABLE 2

| Day # | GUR (mg/hr) | $\Delta DO$ (%) | Ab (mg/day) |
|---|---|---|---|
| 1 | 9.570 | | |
| 2 | | | |
| 3 | 37.200 | | 1.920 |
| 4 | 50.900 | | |
| 5 | 66.000 | | 8.640 |
| 6 | 94.460 | | |
| 7 | 110.750 | 14.000 | 32.160 |
| 8 | | | |
| 9 | | | |
| 10 | 155.700 | 11.600 | 47.520 |
| 11 | 148.800 | 15.200 | |
| 12 | 161.200 | 13.300 | 64.320 |

TABLE 2-continued

| Day # | GUR (mg/hr) | ΔDO (%) | Ab (mg/day) |
|---|---|---|---|
| 13 | 149.800 | 13.200 | |
| 14 | 145.500 | 12.100 | 90.480 |
| 15 | | | |
| 16 | | | |
| 17 | 137.500 | 11.300 | |
| 18 | 143.900 | | 124.560 |
| 19 | | | |
| 20 | 168.600 | | |
| 21 | 168.000 | 26.400 | 135.120 |
| 22 | | | |
| 23 | | | |
| 24 | 115.600 | 24.700 | |
| 25 | 127.450 | 33.500 | 135.120 |
| 26 | 142.200 | 34.100 | |
| 27 | 153.180 | 33.100 | |
| 28 | 156.900 | 27.200 | 140.400 |
| 29 | | | |
| 30 | | | |
| 31 | 155.290 | 38.600 | 151.440 |
| 32 | 145.600 | 34.300 | |
| 33 | 145.600 | 34.300 | 156.960 |
| 34 | 146.000 | 28.500 | |
| 35 | 146.850 | 30.900 | 162.720 |
| 36 | | | |
| 37 | | | |
| 38 | 147.700 | 32.800 | 168.480 |
| 39 | 147.200 | | |
| 40 | 148.100 | 34.100 | 204.936 |
| 41 | 149.380 | 31.900 | |
| 42 | 149.380 | 29.400 | 189.600 |
| 43 | | | |
| 44 | | | |
| 45 | 151.500 | 32.000 | 194.664 |
| 46 | 151.500 | 27.100 | |
| 47 | 151.500 | 35.400 | 179.736 |
| 48 | 153.100 | 32.100 | |
| 49 | 153.300 | 29.400 | 179.736 |

The basal medium feed rate was manipulated to establish and maintain a target GUR of 150 mg/hr. By day 10 the GUR stabilized significantly, and by day 22, the antibody production [Ab] and ΔDO stabilized too. The production phase following immediately was maintained for four weeks, during which, the antibody production to ΔDO ratio exhibited relative constancy.

The goals of this run were to demonstrate an ability to culture this suspension type cell in the invention, and to manufacture enough antibody to meet in house research requirements. Having met these objectives, the run was terminated.

EXAMPLE III

The propagation of a suspension type cell line in the invention is described in this example to illustrate improved productivity by means of controlling the effects of product and metabolite feedback inhibition. The cell line is a murine hybridoma that secretes monoclonal antibodies against TGEV. The IgG$_{2a}$ antibody product in the culture supernatant is measured by RID assay.

The culture system was sterilized, assembled, connected to accessories and chamber controls, primed and flushed, as generally described in "The Method of the Invention" section.

The process parameters in the culture system were set to establish start up conditions. The set point for the temperature controller 703 was set at 37° C. The gas flow meters 609 were adjusted such that the pH monitor 704 read 7.3. Nitrogen flowrate in this run was set to zero. DO monitors 702 were excluded in this run. The loop circulation controller 705 was set to obtain a loop circulation rate of 350 ml/min. The programmable controller 701 was set to deliver ECS feed medium (and collect ECS product) at a frequency of 6 times/day and a volume of 24 ml/day. This volumetric feed rate was varied through the run as described below.

An inoculum containing $3 \times 10^8$ cells was pumped into the ECS of the bioreactor as generally described in "The Method of the Invention" section. A 1.4m$^2$ surface area bioreactor (model 1-L, C.D. Medical Inc.) 201 was used in this run. The growth factor mixture comprised 35% fetal bovine serum, 1% penicillin streptomycin, in DME high glucose basal medium. This composition was varied through the run as described below. The ECS feed reservoir 101 and ECS product reservoir 102 were replaced three times/week throughout the run.

The basal medium feed pump controller 706 was set to deliver 41.5 ml/hr. The basal feed medium comprised 2% L-glutamine, 1% penicillin streptomycin, in DME high glucose basal medium. This composition was maintained throughout the run. Thus, the optional separate glucose feed system was not used in this run. The basal medium feed reservoir 402 was replaced 3 times/week, and the waste reservoir 401 was replaced when necessary.

Samples were withdrawn regularly for off line glucose analysis, as generally described in "The Method of the Invention" section. As Table 3(a) shows, the GUR and ΔDO both increased as the cells proliferated in the ECS of the bioreactor 201.

TABLE 3(a)

| Day # | GUR (mg/hr) | ECS (ml/day) | Ab (mg/day) |
|---|---|---|---|
| 1 | 12.0 | 24 | |
| 2 | 31.9 | 24 | |
| 3 | | 24 | |
| 4 | 45.2 | 24 | 17.28 |
| 5 | 52.7 | 24 | |
| 6 | 53.5 | 24 | 50.40 |
| 7 | 83.8 | 24 | |
| 8 | 100.4 | 24 | 43.68 |
| 9 | 91.7 | 24 | |
| 10 | 100.0 | 24 | |
| 11 | 103.8 | 24 | 80.16 |
| 12 | 84.2 | 24 | |
| 13 | 88.5 | 24 | 88.32 |
| 14 | 82.9 | 24 | |
| 15 | 80.8 | 24 | 88.32 |
| 16 | | 24 | |
| 17 | | 24 | |
| 18 | 81.2 | 24 | 88.32 |
| 19 | 85.7 | 24 | |
| 20 | 100.1 | 24 | 88.32 |
| 21 | 105.2 | 24 | |
| 22 | 109.7 | 24 | 96.48 |
| 23 | | 24 | |
| 24 | 105.8 | 24 | |
| 25 | | 24 | |
| 26 | 104.0 | 24 | 121.44 |
| 27 | 102.1 | 30 | |
| 28 | 103.4 | 30 | |
| 29 | 103.1 | 30 | 151.80 |
| 30 | | 30 | |
| 31 | | 30 | |
| 32 | 109.1 | 30 | 151.80 |
| 33 | 108.6 | 30 | |
| 34 | | 30 | 130.80 |
| 35 | 110.7 | 42 | |
| 36 | 112.8 | 42 | 168.84 |
| 37 | | 42 | |
| 38 | | 42 | |
| 39 | 114.6 | 42 | 168.84 |
| 40 | 114.6 | 42 | |
| 41 | 114.6 | 42 | 154.56 |
| 42 | | 42 | |
| 43 | 113.1 | 42 | 153.72 |
| 44 | | 54 | |
| 45 | | 54 | |
| 46 | 114.3 | 54 | 163.08 |

TABLE 3(a)-continued

| Day # | GUR (mg/hr) | ECS (ml/day) | Ab (mg/day) |
|---|---|---|---|
| 47 | 113.7 | 54 | |
| 48 | 113.7 | 54 | 163.08 |
| 49 | 114.6 | 54 | |
| 50 | 114.6 | 54 | 163.08 |
| 51 | | 60 | |
| 52 | | 60 | |
| 53 | 114.9 | 60 | 162.00 |
| 54 | 115.5 | 60 | |
| 55 | 115.5 | 60 | 162.00 |

The basal medium feed rate was manipulated to establish and maintain a target GUR of 100 mg/hr. By day 8 the GUR stabilized significantly, and by day 26, the antibody production stabilized too.

The production phase following immediately was maintained for almost four weeks. During this period, the ECS volumetric feed rate (and ECS product collection rate) was maintained at 30,42 and 54 ml/day, each for at least a week. The fetal bovine serum content of the growth factor mixture was adjusted to ensure constant serum feed to the system. As Table 3(b) shows, while the increase in ECS feed rate had no effect upon GUR, it improved the antibody productivity by 45%.

TABLE 3(b)

| ECS (ml/day) | Ab (mg/day) |
|---|---|
| OLDER RUN | |
| 24.000 | 112.800 |
| 24.000 | 96.000 |
| 24.000 | 108.000 |
| 36.000 | 162.000 |
| 36.000 | 154.800 |
| 36.000 | 144.000 |
| 36.000 | 144.000 |
| 36.000 | 144.000 |
| 48.000 | 139.200 |
| CURRENT RUN | |
| 24.000 | 96.480 |
| 24.000 | 121.440 |
| 30.000 | 151.800 |
| 30.000 | 151.800 |
| 30.000 | 130.800 |
| 42.000 | 168.840 |
| 42.000 | 168.840 |
| 42.000 | 154.560 |
| 42.000 | 153.720 |
| 54.000 | 163.080 |
| 54.000 | 163.080 |
| 54.000 | 163.080 |
| 60.000 | 162.000 |
| 60.000 | 162.000 |

Thus, the effects of product and metabolite feedback inhibition were overcome by maintaining a higher ECS product collection rate (or ECS feed rate). The combined results of this exercise and that from another run are reported in Table 3(b). It was concluded that for the given set of process conditions, the ECS feed rate must be set to at least 42 ml/day to maximize antibody productivity.

The goal of this run was to illustrate improved productivity by means of controlling the effects of product and metabolite feedback inhibition. Having met this objective, the run was terminated.

EXAMPLE IV

The propagation of a suspension type cell line in the invention is described in this example to illustrate improved process control by means of an optional separate glucose feed system. The cell line is a murine hybridoma that secretes monoclonal antibodies against TGEV. The $IgG_{2a}$ antibody product in the culture supernatant is measured by RID assay.

The culture system was sterilized, assembled, connected to accessories and chamber controls, primed and flushed, as generally described in "The Method of the Invention" section.

The process parameters in the culture system were set to establish start up conditions. The set point for the temperature controller 703 was set at 37° C. The gas flow meters 609 were adjusted such that the pH monitor 704 read 7.2, and the DO monitors 702 read about 95% air saturation. Nitrogen flowrate in this run was set to zero. The loop circulation controller 705 was set to obtain a loop circulation rate of 350 ml/min. The programmable controller 701 was set to deliver ECS feed medium (and collect ECS product) at a frequency of 6 times/day and a volume of 35 ml/day.

An inoculum containing $3 \times 10^8$ cells was pumped into the ECS of the bioreactor 201 as generally described in "The Method of the Invention" section. A 2.0 $m^2$ surface area bioreactor (model FC-20, Toray Industries) was used in this run. The growth factor mixture comprised 24% fetal bovine serum, 1% penicillin streptomycin, in DME glucose free basal medium. This ECS feed composition was maintained throughout the run. The ECS feed reservoir 101 and ECS product reservoir 102 were replaced three times/week throughout the run.

The basal medium feed pump controller 706 was set to deliver 42 ml/hr. The basal feed medium comprised 2% L-glutamine, 1% penicillin streptomycin, in DME glucose free basal medium. This composition was maintained throughout the run. The programmable controller 701 was set to deliver glucose, via the glucose feed pump 405, such that the effective glucose concentration in the feed medium (Gi) was 1198 mg/l. The glucose reservoir 404 contained glucose stock solution at 200 g/l. The basal medium feed reservoir 402 was replaced 3 times/week, the glucose reservoir was replaced 1 time/week, and the waste reservoir 401 was replaced when necessary.

Samples were withdrawn regularly for off line glucose analysis, as generally described in "The Method of the Invention" section. As shown in Table 4 below, the Gi was manipulated via the programmable controller 701, to support the increasing GUR and $\Delta DO$ of the proliferating cells in the bioreactor 201, and at the same time maintain an approximately constant system glucose concentration (Go) of 800 mg/l.

TABLE 4

| Day # | Gi (mg/l) | Go (mg/l) | GUR (mg/hr) | ΔDO (%) | Ab (mg/day) |
|---|---|---|---|---|---|
| 1 | 1198 | 790.0 | 17.1 | | |
| 2 | 2001 | 770.0 | 51.6 | 6.2 | |
| 3 | 2489 | 840.0 | 69.3 | 9.6 | |
| 4 | 2716 | 840.0 | 79.0 | 11.2 | |
| 5 | 2845 | 830.0 | 84.8 | 12.1 | |
| 6 | 2923 | 830.0 | 88.1 | 13.7 | |
| 7 | 2975 | 780.0 | 92.4 | 16.1 | 40.950 |
| 8 | 3148 | 840.0 | 97.4 | 18.0 | |
| 9 | 2606 | 360.0 | 94.3 | 18.6 | 62.300 |
| 10 | 2489 | 270.0 | 93.2 | 21.0 | |
| 11 | | | | | |
| 12 | 2489 | 240.0 | 94.5 | 22.6 | 82.950 |
| 13 | 2489 | 210.0 | 95.7 | 25.1 | |
| 14 | 2489 | 157.0 | 97.9 | 29.6 | 93.100 |
| 15 | 2489 | 123.0 | 99.4 | 33.1 | |
| 16 | 2489 | 107.0 | 100.0 | 33.5 | 115.150 |
| 17 | | | | | |
| 18 | 2489 | 86.0 | 100.9 | 35.1 | |

TABLE 4-continued

| Day # | Gi (mg/l) | Go (mg/l) | GUR (mg/hr) | ΔDO (%) | Ab (mg/day) |
|---|---|---|---|---|---|
| 19 | 2489 | 86.0 | 100.9 | 35.6 | 127.050 |
| 20 | 2489 | 80.0 | 101.2 | 37.1 | |
| 21 | 2489 | 68.0 | 101.7 | 38.1 | 133.000 |
| 22 | 2489 | 68.0 | 101.7 | 38.6 | |
| 23 | 2489 | 51.0 | 102.4 | 40.6 | 133.000 |
| 24 | | | | | |
| 25 | | | | | |
| 26 | 2489 | 49.0 | 102.5 | 41.0 | 144.900 |
| 27 | 2489 | 53.0 | 102.3 | 43.0 | |
| 28 | 2489 | 48.0 | 102.5 | 44.1 | 148.750 |
| 29 | 2489 | 50.0 | 102.4 | | |
| 30 | 2489 | 48.0 | 102.5 | 41.6 | 154.000 |
| 31 | | | | | |
| 32 | | | | | |
| 33 | 2489 | 47.0 | 102.5 | 44.6 | 154.000 |
| 34 | 2489 | 51.0 | 102.4 | 44.7 | |
| 35 | 2489 | 49.0 | 102.5 | 45.1 | 148.750 |

By day 8 the GUR reached a target value of 100 mg/hr, at which point, the glucose pump was momentarily shut off to rapidly bring Go down to 300 mg/l. Then, the programmable controller 701 was reset to obtain a Gi of 2489 mg/l, to support the established GUR of 100 mg/hr, and at the same time allow the Go to settle below 1 mM (or 180 mg/l).

The basal medium feed pump controller 706 was set to deliver 42 ml/hr from the beginning of the run, a basal medium feed rate that can support a GUR of 150 mg/hr. However, immediately following the Go manipulation on day 8, the GUR levelled at 100 mg/hr, and ΔDO at 22%, as a result of glucose limitation (200 mg/l <Go<300 mg/l). Thus, a separate glucose feed system made possible an independent and useful control of the process. After day 14, further glucose limitation (Go<180 mg/l) led to an increasingly aerobic GUR as a result of the Pasteur shift in cell metabolism. Thus, over the next three weeks, although the GUR remained relatively unchanged at 100 mg/hr, the ΔDO eventually stabilized at 44%. The antibody production stabilized at 154 mg/hr, which is comparable to production values obtained under similar process conditions but non limiting glucose values (Go>300 mg/l), as seen in Example 3.

The goal of this run was to demonstrate an improved ability to control the process by means of using a separate glucose feed system. Having met this objective, the run was terminated at this point.

We claim:

1. A hollow fiber cell propagation system comprising:
    (i) a hollow fiber bioreactor including nutrient permeable hollow fibers positioned in an extracapillary space;
    (ii) a first loop connected to a first inlet and a first outlet of said bioreactor so as to provide and change flow of fluids through lumens of said fibers, said first loop comprising:
        (a) pump means for circulating fluids through said first loop;
        (b) means for introducing gases into said first loop;
        (c) means for determining and changing the temperature of the fluids in said first loop;
        (d) means for determining the dissolved oxygen content of said fluids in said first loop upstream or downstream of said bioreactor, said dissolved oxygen determining means being positioned in flow block means with a sensing portion of said dissolved oxygen determining means positioned in said flow block means so as to be in contact with fluid flowing in said first loop, said flow block means including sterile filter means for passing calibrating gas into said flow block means so as to be in contact with said sensing portion for calibrating said dissolved oxygen determining means at a pressure equal to that of the fluid flowing in said first loop;
        (e) means for determining and changing the flow rate of said fluids through said first loop;
        (f) means for determining and changing pH of said fluids in said first loop;
        (g) means for introducing fluids comprising reagents and basal medium containing nutrient into said first loop; and
    (iii) a second loop connected to a second inlet and a second outlet of said bioreactor so as to provide and change flow of fluids through said extracapillary space.

2. A hollow fiber cell propagation system as defined by claim 1 in which said means for introducing fluids provides for introduction of said basal medium and reagents into said first loop at a rate determined by a preselected nutrient utilization rate in said bioreactor.

3. A hollow fiber cell propagation system as defined by claim 1 in which said second loop (iii) comprises means for simultaneous introduction of fluids into and removal of product from said extracapillary space at determined rates.

4. A hollow fiber cell propagation system as defined by claim 1 in which said nutrient permeable hollow fibers are formed of a synthetic polymer.

5. A hollow fiber cell propagation system as defined by claim 4 in which said synthetic polymer is formed from a polymethylmethacrylate, a polysulfone or a cellulose derivative.

6. A hollow fiber cell propagation system as defined by claim 1 in which said means (ii)(c) for determining and changing the temperature of said fluids comprises a resistance temperature probe positioned in a resistance temperature probe flow block means that is included as a portion of said first loop, said resistance temperature probe being connected to an electronic monitor and controller, said controller including means to compare the signal from said resistance temperature probe with a preselected set point.

7. A hollow fiber cell propagation system as defined by claim 1 in which said means (ii)(c) for determining and changing the temperature of said fluids comprises a resistance heated conduit as a portion of said first loop through which said fluids flow.

8. A hollow fiber cell propagation system as defined by claim 1 in which said means (ii)(c) for determining and changing the temperature of said fluids comprises an etched foil resistance heating element as a portion of said first loop.

9. A hollow fiber cell propagation system as defined by claim 1 in which said means for determining the dissolved oxygen content of said fluids determines the dissolved oxygen content both upstream and downstream of said bioreactor.

10. A hollow fiber cell propagation system as defined by claim 9 further comprising means for determining the difference between the dissolved oxygen content of said fluids upstream and downstream of said bioreactor.

11. A hollow fiber cell propagation system as defined by claim 9 further comprising means for determining the difference between the dissolved oxygen content of said fluids upstream and downstream of said bioreactor and for utilizing said difference to determine the aerobic efficiency and provide a real time verification and measurement of cell metabolism in said bioreactor.

12. A hollow fiber cell propagation system as defined by claim 11 further comprising means for utilizing the difference in the dissolved oxygen content of said fluids upstream and downstream of said bioreactor to assess the performance of said bioreactor.

13. A hollow fiber cell propagation system as defined by claim 1 further including a programmable controller means constructed and arranged so as to control said means (ii) (e) for determining and changing the flow rate of said fluids through said first loop.

14. A hollow fiber cell propagation system as defined by claim 13 in which said programmable controller means receiving data provided by nutrient and ammonia analyzers using fluid from said first loop controls introduction of basal medium into said first loop.

15. A hollow fiber cell propagation system as defined by claim 1 in which said means ii(b) for introducing gases into said first loop further comprises an oxygenator means for introducing gases into basal medium after oxygen depletion due to passage through said bioreactor.

16. A hollow fiber cell propagation system as defined by claim 15 in which said oxygenator means includes means for blending air, nitrogen and carbon dioxide prior to introduction into the basal medium.

17. A hollow fiber cell propagation system as defined by claim 15 in which said oxygenator means comprises a plurality of semipermeable hollow fibers membranes capable of passing gas to the basal medium.

18. A hollow fiber cell propagation system as defined by claim 1 further comprising a waste disposal means for automatically displacing from said first loop a volume substantially identical to the volume of fresh basal medium introduced into said first loop.

19. A hollow fiber cell propagation system as defined by claim 1 in which said means (ii) (d) for determining and changing the dissolved oxygen content of said fluids comprises said flow block means further including a window in a wall of said flow block means through which said sensing portion of said dissolved oxygen determining probe may be observed.

20. A hollow fiber cell propagation system as defined by claim 9 further comprising means for determining the value of the expression GUR/$\Delta$DO where GUR means glucose utilization rate and $\Delta$DO means dissolved oxygen differential.

21. A hollow fiber cell propagation system defined by claim 20 further comprising means for using said GUR/$\Delta$DO value to determine aerobic efficiency of said system.

22. A hollow fiber cell propagation system as defined by claim 11 or claim 20 further comprising means for utilizing the difference in dissolved oxygen content upstream and downstream of said bioreactor to assess the efficiency of cell production by said bioreactor.

23. A hollow fiber cell propagation system as defined by claim 1 in which said means (ii)(b) for introducing gases comprises oxygenator means having a plurality of permeable hollow fibers positioned in an extracapillary space for passing oxygen depleted fluid in said first loop through the lumens of said hollow fibers and means for passing air, oxygen and nitrogen or a blend thereof into and through said extracapillary space for introduction into said oxygen depleted fluid in the lumens of said hollow fibers.

24. A hollow fiber cell propagation system as defined by claim 23 further comprising means for controlling the oxygen content of said fluid in said first loop.

25. A hollow fiber cell propagation system as defined by claim 23 or claim 24 further comprising means for controlling the amount of air, carbon dioxide and nitrogen introduced into said fluid in said first loop passing through the lumens of said hollow fibers of said oxygenator and thereby regulate the pH and oxygen content of said fluid upon exit from said oxygenator.

26. A hollow fiber cell propagation system as defined by claim 23 further comprising a waste disposal system in line with said oxygenator means, said waste disposal system including valve means to preclude siphoning of waste fluid back into said first loop.

27. A hollow fiber cell propagation system as defined by claim 1 further comprising a programmable controller means to control said means (ii)(g) for introducing fluids into said first loop, and for changing flow in said second loop.

28. A process for the conversion of a raw material to a useful product by cell metabolism which comprises
  (i) inoculating the extracapillary space of a hollow fiber bioreactor with cells and a growth factor mixture for said cells;
  (ii) circulating basal medium comprising a nutrient into and through the lumens of the hollow fibers of said bioreactor;
  (iii) measuring dissolved oxygen content of said circulating basal medium before and after passage through said bioreactor with dissolved oxygen content determining means while said circulating basal medium is in a fluid flow loop including said lumens of said hollow fibers of said bioreactor;
  (iv) calibrating said dissolved oxygen determining means while said dissolved oxygen determining means is positioned in flow block means with a sensing portion of said dissolved oxygen determining means positioned in said flow block means so as to be in contact with fluid flowing in said fluid flow loop when said dissolved oxygen determining means is not being calibrated, passing calibrating gas into said flow block means so as to be in contact with said sensing portion for calibrating said dissolved oxygen determining means at a pressure equal to that of fluid flowing in said fluid flow loop;
  (v) introducing oxygen into said circulating basal medium to establish and maintain an oxygen content sufficient to support aerobic metabolism of said cells;
  (vi) utilizing the differential in dissolved oxygen content of the circulating basal medium before and after passage through the lumens of the hollow fibers of said bioreactor to determine aerobic efficiency and provide a real time verification and measurement of cell metabolism in said bioreactor.

29. A process as defined by claim 28 in which oxygen is introduced into said circulating basal medium in step (iii) by passage of said circulating basal medium through the lumens of a hollow fiber oxygenator in which gases containing oxygen are present in the extracapillary space surrounding said hollow fibers of said oxygenator.

30. A process as defined by claim 28 further comprising simultaneously introducing said growth factor into and removing product from said extracapillary space of said hollow fiber bioreactor at rates which do not differ by more than about five percent.

31. A process as defined by claim 28 in which said nutrient is maintained at a level of not more than about one millimolar in said bioreactor.

32. A process as defined by claim 28 in which said nutrient is glucose.

33. A process as defined by claim 28 in which said conversion is accomplished by mammalian, insect, avian, plant or fungal cells.

34. A process is defined by claim 28 in which said conversion is accomplished by anchorage dependent cells.

35. A process as defined by claim 28 in which said conversion in accomplished by suspension cells.

36. A process as defined by claim 28 in which said conversion is accomplished by cells which yield a viral protein.

37. A process as defined by claim 35 in which said conversion is accomplished by a hybridoma.

38. A process as defined by claim 28 in which the rate of circulation of said basal medium into and through the lumens of said hollow fibers in said bioreactor is controlled to provide a predetermined bioreactor nutrient utilization rate.

39. A process as defined by claim 28 in which said nutrient is glucose and in which the concentration of said glucose is maintained at a level of not more than about one millimolar in said bioreactor.

40. A process as defined by claim 28 in which the adverse effects of product and metabolite feedback inhibition are ameliorated by control of rate at which (i) fluids are introduced into said extracapillary space or (ii) product is removed from said extracapillary space.

41. A process as defined by claim 28 in which the temperature in said bioreactor is maintained at about 37° C.

42. A process as defined by claim 28 in which samples from said circulating basal medium are subjected to ammonia and nutrient analyses and the data from such analyses is used to determine a rate of introduction of basal medium.

43. A process as defined by claim 42 in which said nutrient is glucose and said data is used to determine the rate of introduction of basal medium required to provide a preselected glucose utilization rate.

44. A process as defined by claim 42 in which said conversion is accomplished by an anchorage dependent or suspended mammalian cells.

45. A hollow fiber process for the conversion of a raw material by cell metabolism which comprises
    (i) inoculating the extracapillary space of a hollow fiber bioreactor with cells and a growth factor for said cells;
    (ii) passing basal medium and nutrients from a storage vessel into and through the lumens of said hollow fibers;
    (a) the rate of passage of said medium and reagents through said lumens being controlled to provide a preselected bioreactor glucose utilization rate;
    (iii) measuring dissolved oxygen content of said circulating basal medium before and after passage through said bioreactor with dissolved oxygen content determining means while said circulating basal medium is in a fluid flow loop including said lumens of said hollow fibers of said bioreactor, said dissolved oxygen content determining means including means for calibrating said dissolved oxygen content determining means at the same pressure as fluid flowing in said fluid flow loop;
    (iv) calibrating said dissolved oxygen determining means while said dissolved oxygen determining means is positioned in flow block means with a sensing portion of said dissolved oxygen determining means positioned in said flow block means so as to be in contact with fluid flowing in said fluid flow loop when said dissolved oxygen determining means is not being calibrated, passing calibrating gas into said flow block means so as to be in contact with said sensing portion for calibrating said dissolved oxygen determining means at a pressure equal to that of fluid flowing in said fluid flow loop;
    (v) introducing oxygen into said basal medium and nutrients in a predetermined amount sufficient to support aerobic metabolism of said cells;
    (vi) determining the differential in the dissolved oxygen content of said basal medium and nutrients upstream and downstream of said bioreactor;
    (vii) utilizing said dissolved oxygen differential to determine the aerobic efficiency of the cell metabolism in the bioreactor and to provide a real time verification and measurement of said cell metabolism; and
    (viii) simultaneously introducing growth factor into and removing product from said extracapillary space at rates which do not differ by more than about 5%.

46. A process as defined by claim 45 in which said conversion is accomplished by mammalian cells and in which the basal medium comprises glucose.

47. A process as defined by claim 46 in which said mammalian cells are anchorage dependent.

48. A process as defined by claim 46 in which said mammalian cells are suspended.

49. A process for conversion of a raw material into a useful product by cell metabolism which comprises:
    (i) inoculating the extracapillary space of a hollow fiber bioreactor with cells and a growth factor for said cells;
    (ii) circulating basal medium comprising a nutrient into and through the lumens of the hollow fibers of said bioreactor;
    (iii) measuring dissolved oxygen content of said circulating basal medium before and after passage through said bioreactor with dissolved oxygen content determining means while said lumens of said hollow fibers of said bioreactor;
    (iv) calibrating said dissolved oxygen determining means while said dissolved oxygen determining means is positioned in flow block means with a sensing portion of said dissolved oxygen determining means positioned in said flow block means so as to be in contact with fluid flowing in said fluid flow loop when said dissolved oxygen determining means is not being calibrated, passing calibrating gas into said flow block means so as to be in contact with said sensing portion for calibrating said dissolved oxygen determining means at a pressure equal to that of fluid flowing in said fluid flow loop;
    (v) introducing oxygen into said circulating basal medium to establish and maintain an oxygen content sufficient to support aerobic metabolism of said cells; and
    (vi) simultaneously measuring the glucose utilization rate (GUR) of said bioreactor and the dissolved oxygen ($\Delta DO$) differential across said bioreactor and using the GUR/ΔDO ratio to assess the bioreactor cell production efficiency of said bioreactor.

50. A process as defined by claim 49 in which said GUR/ΔDO ratio is maintained at 3 to 6 milligrams per hour.

51. A process as defined by claim 49 in which steps (ii) and (iii) are conducted in response to a programmable controller.

52. A process as defined by claim 50 in which feedback inhibition is precluded by a programmable controller.

53. A process for the conversion of a raw material into a useful product by cell metabolism which comprises:
   (i) inoculating the extracapillary space of a hollow fiber bioreactor with cells and a growth factor for said cells;
   (ii) introducing a glucose free basal medium into a means for circulating fluids through the lumens of the hollow fibers of said bioreactor;
   (iii) separately introducing glucose into said means for circulating fluids through the lumens of said hollow fibers of said bioreactor;
   (iv) measuring dissolved oxygen content of said circulating basal medium before and after passage through said bioreactor with dissolved oxygen content determining means while said circulating basal medium is in a fluid flow loop including said lumens of said hollow fibers of said bioreactor;
   (v) calibrating said dissolved oxygen determining means while said dissolved oxygen determining means is positioned in flow block means with a sensing portion of said dissolved oxygen determining means positioned in said flow block means so as to be in contact with fluid flowing in said fluid flow loop when said dissolved oxygen determining means is not being calibrated, passing calibrating gas into said flow block means so as to be in contact with said sensing portion for calibrating said dissolved oxygen determining means at a pressure equal to that of fluid flowing in said fluid flow loop;
   (vi) introducing oxygen into said circulating basal medium to establish and maintain an oxygen content sufficient to support aerobic metabolism of said cells; and
   (vii) simultaneously measuring the glucose utilization rate (GUR) of said bioreactor and the dissolved oxygen (ΔDO) differential across said bioreactor and using the GUR/ΔDO ratio to assess the bioreactor cell production efficiency of said bioreactor.

54. A process as defined by claim 53 further comprising: (viii) monitoring and controlling one or more of steps (i) through (vii) with a programmable controller.

55. A hollow fiber process for the conversion of raw material by cell metabolism which comprises
   (i) inoculating the extracapillary space of a hollow fiber bioreactor will cells and a growth factor for said cells;
   (ii) passing basal medium and nutrients from a storage vessel into and through the lumens of said hollow fibers;
   (a) the rate of passage of said medium and reagents through said lumens being controlled to provide a selected bioreactor glucose utilization rate;
   (iii) measuring dissolved oxygen content of said circulating basal medium before and after passage through said bioreactor with dissolved oxygen content determining means while said circulating basal medium is in a fluid flow loop including said lumens of said hollow fibers of said bioreactor;
   (iv) calibrating said dissolved oxygen determining means while said dissolved oxygen determining means is positioned in flow block means with a sensing portion of said dissolved oxygen determining means positioned in said flow block means so as to be in contact with fluid flowing in said fluid flow loop when said dissolved oxygen determining means is not being calibrated, passing calibrating gas into said flow block means so as to be in contact with said sensing portion for calibrating said dissolved oxygen determining means at a pressure equal to that of fluid flowing in said fluid flow loop;
   (v) introducing oxygen into said basal medium and nutrients in a predetermined amount sufficient to support aerobic metabolism of said cells;
   (vi) simultaneously measuring the glucose utilization rate (GUR) of said bioreactor and the dissolved oxygen (ΔDO) differential across said bioreactor and using the GUR/ΔDO ratio to assess the bioreactor cell production efficiency of said bioreactor; and
   (vii) monitoring and controlling one or more of steps (i) through (vi) with a programmable controller.

* * * * *